United States Patent [19]

Thomas

[11] Patent Number: 4,784,120
[45] Date of Patent: Nov. 15, 1988

[54] ARM CONSTRAINT

[76] Inventor: Rebecca A. Thomas, 361 Villa Ave., Buffalo, N.Y. 14216

[21] Appl. No.: 910,534

[22] Filed: Sep. 23, 1986

[51] Int. Cl.$^4$ .............................................. A61F 5/01
[52] U.S. Cl. ...................................... 128/77; 248/118; 269/328
[58] Field of Search ................. 128/27, 26, 88 R, 133, 128/134, 88, 68; 248/118; 269/322, 328

[56] References Cited

U.S. PATENT DOCUMENTS

| | | | |
|---|---|---|---|
| 1,376,280 | 4/1921 | James | 248/118 |
| 2,477,898 | 8/1949 | Rehman et al. | 248/118 |
| 3,124,328 | 3/1964 | Kortsch | 248/118 |
| 3,295,518 | 1/1967 | Hazlewood et al. | 128/133 |
| 3,381,684 | 5/1968 | Anderson | 128/68 |
| 3,707,963 | 1/1973 | Keropian | 128/77 |
| 4,149,532 | 4/1979 | Terry et al. | 128/77 |
| 4,237,873 | 12/1980 | Terry et al. | 128/77 |
| 4,259,949 | 4/1981 | Axelsson | 128/77 |
| 4,370,976 | 2/1983 | Wanchik et al. | 128/77 |
| 4,604,997 | 8/1986 | De Bastiani et al. | 128/77 X |
| 4,612,919 | 9/1986 | Best | 128/77 |
| 4,660,550 | 4/1987 | Bodine | 128/77 |

Primary Examiner—David A. Wiecking
Assistant Examiner—Moshe I. Cohen
Attorney, Agent, or Firm—Bean, Kauffman & Bean

[57] ABSTRACT

An arm constraint particularly adapted for use as an aid in the self-feeding of a person afflicated with tremors. The constraint generally includes a base adapted for mounting on a suitable support, such as a table or hospital bedside tray; a forearm rest defining a forearm rest surface; means for supporting the forearm rest on the base for rotation about a first vertically disposed axis and for arranging the rest surface in a horizontally disposed position selectively vertically adjustable relative to the base; a hand rest; mounting means for connecting the hand rest to an end of the forearm rest for rotation relative thereto about a second horizontally disposed axis; a constraint for removably retaining a forearm in engagement with the rest surface with a hand arranged for overlying engagement with the hand rest; a plate supporting table; and mounting means for mounting the plate supporting table on the base to underlie the hand rest and for vertical adjustment relative thereto. The manual force required to rotate the forearm rest and the hand rest about the first and second axes may be selectively and individually varied.

10 Claims, 1 Drawing Sheet

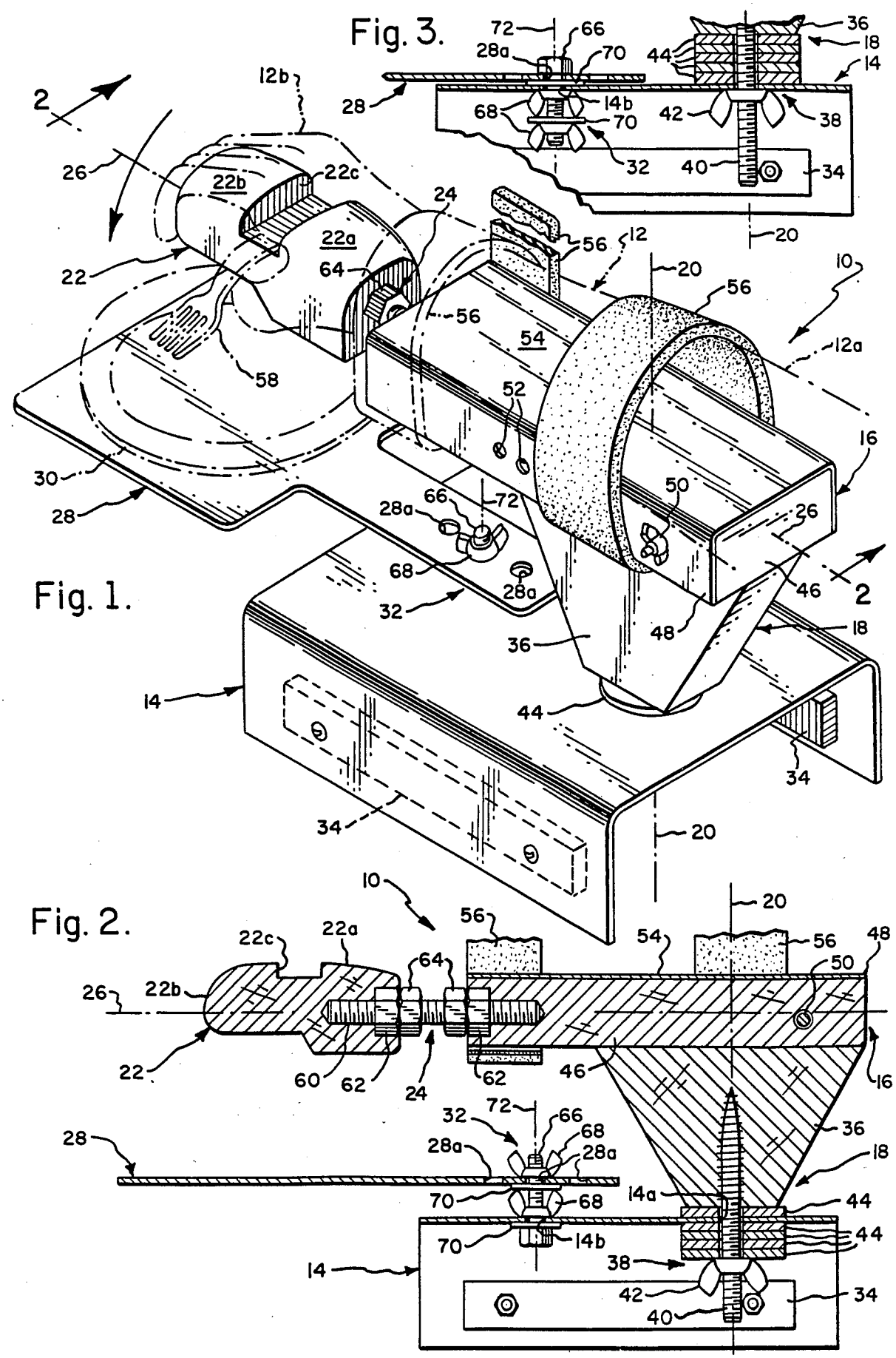

ARM CONSTRAINT

BRIEF DESCRIPTION OF THE PRIOR ART

Heretofore, various efforts have been made to devise arm constraints for use by patients subject to uncontrolled tremors with a view towards assisting such patients to feed themselves. As by way of example, reference may be made to U.S. Pat. Nos. 4,149,532 and 4,259,949.

BRIEF DESCRIPTION OF THE INVENTION

The present invention is directed towards an arm constraint adapted to stabilize and guide the arm of a patient subject to arm tremors, so as to allow the patient to feed himself.

More particularly, in accordance with a preferred form of the invention, the arm constraint is adapted to be supported on any convenient supporting surface, such as may be defined by a table or a patient's bedside tray stand, to allow the patient to feed himself while in a seated or partially reclined position, as desired. The portable nature of the arm constraint allows for its removal so as to clear the supporting surface for other uses when the patient has finished eating.

The present arm constraint serves to effectively constrain the forearm and hand of a patient against transverse, lengthwise and vertical displacements, while allowing the hand to be swung about both a horizontal axis extending lengthwise of the forearm and a vertical axis extending through the forearm adjacent the patient's elbow. As a result, a person is constrained to move an eating implement along an inclined, arcuate path to permit food to be picked up from a plate and elevated to the patient's mouth and the implement to be subsequently returned to the plate.

Further, the present arm constraint allows for individual adjustments of forces required to be exerted by a patient to swing his hand about the horizontal and vertical axes and for adjustments in the height of the patient's forearm and hand relative to the constraint supporting surface, as well as their distance from a food-containing plate independently supported by the base of the arm constraint.

BRIEF DESCRIPTION OF THE DRAWINGS

The nature and mode of operation of the present invention will now be more fully described in the following detailed description taken with the accompanying drawings wherein:

FIG. 1 is a perspective view of a constraint formed in accordance with a preferred form of the present invention;

FIG. 2 is a sectional view taken generally along the line 2—2 in FIG. 1; and

FIG. 3 is a fragmentary sectional view similar to FIG. 2 showing parts in an alternative adjusted position.

DETAILED DESCRIPTION

Reference is first made to FIG. 1, wherein an arm constraint formed in accordance with a preferred form of the present invention is designated as 10 and shown in operative association with a human arm 12 including a forearm 12a and a hand 12b.

Constraint 10 generally comprises a suitable base 14; a forearm rest 16 for supporting forearm 12a; means 18 for supporting forearm rest 16 above base 14 and for rotation about a vertically disposed first axis 20; a hand rest 22 for supporting hand 12b; mounting means 24 for supporting hand rest 22 adjacent one end of forearm rest 16 for rotation about a horizontally disposed second axis 26; a table 28 for supporting a plate or bowl 30; and mounting means 32 for supporting table 28 in underlying relation to hand rest 22.

Base 14 is intended to be placed on a table or bedside tray stand, not shown, as may be convenient for a person desiring to employ arm constraint 10 to aid in his eating of food from plate 30. Base 14 is preferably in the form of an inverted U-shaped metal channel to which are affixed lead bars 34 for the purpose of providing the base with a weight sufficient to prevent movement thereof relative to the surface on which it is supported during use of the constraint. Alternatively, if desired, the present constraint may be provided with means, not shown, to permit clamping of the base in position.

Means 18 is best shown in FIG. 2 as including a pedestal 36 suitably secured to the lower surface of forearm rest 22 and mounting means 28 for mounting the pedestal to upstand from base 14. Mounting means 28 is shown as including a bolt 40, which is threadably attached to pedestal 36 and arranged to project downwardly through a bearing opening 14a provided in the upper surface of base 14, a threading clamping device such as defined by wing nut 42; and a plurality of adjustment washers 44. By this arrangement, forearm rest 16 is allowed to swing horizontally about axis 20 and be vertically adjustable relative to base 14 by the selective positioning of washers 44 in the manner shown for example in FIGS. 2 and 3. The manual force required to effect swinging movement of forearm rest 16 may be selectively controlled or varied by adjustments of the tightness of wing nut 42. Preferably, axis 20 is arranged to intersect with forearm rest 16 adjacent the elbow of a patient using constraint 10.

Forearm rest 16 is preferably provided with an elongated first part 46 rigidly affixed to the top of pedestal 36 and an inverted U-shaped second part 48, which may be selectively locked in adjusted positions lengthwise of first part 46 by suitable means such as a bolt fastener 50 removably fitted through pairs of aligned openings 52 formed in the side flanges of second part 48. The upwardly facing surfaces of parts 46 and 48 cooperate to define a forearm support or rest surface 54 whose length may be selectively adjusted to comfortably support the forearm of any particular patient. Any suitable constraint may be provided to releasably maintain a patient's forearm in engagement with support surface 54, but it is preferable to employ pairs of Velcro strips 56 whose opposite ends are attached to first part 46. If desired, suitable padding or cushioning material, not shown, may be suitably attached to the upper surface of second part 48, as an aid to the comfort of a patient.

Hand rest 22 is preferably provided with contoured palm and finger portions 22a and 22b, respectively, shaped to comfortably receive or engage with the palm and fingers of a patient's hand when laid downwardly thereagainst in the manner shown in FIG. 1. As an aid to a patient's use of constraint 10, palm portion 22a may be provided with a transversely extending recess 22c, which is sized to receive the hand portion of an eating implement, such as a fork 58 shown only in FIG. 1.

Hand rest mounting means 24 is shown in FIG. 2 as including an elongated bolt 60 threadably supported within a pair of mounting nuts 62 fixed within facing ends of forearm rest first part 46 and hand rest 22 and a pair of adjustment nuts 64. By this arrangement, the spacing between the hand and forearm rests may be varied and the manual force required to effect swinging movement of hand rest 22 about axis 26 may be adjustably controlled.

Table 28 is shown as being fabricated from a flat metal plate sized to support a plate, bowl or other food container from which food is to be withdrawn by a patient using implement 58. Suitable means, such as a suction cup device, not shown, may be provided to prevent unintended sliding movements of plate 30 relative to the upper surface of table 28.

Table mounting means 32 is best shown in FIGS. 2 and 3 as including a threaded bolt 66 removably received within bearing openings 14b and 28a provided in the upper flange of base 14 and table 28, and adjustment means defined by a pair of wing nuts 68 and a pair of washers 70. As will be apparent from viewing FIGS. 2 and 3, the vertical distance between table 28 and base 14, as well as hand rest 22, may be varied by selective placements of wing nuts 68 and washers 70. Also, table 28 may be swung horizontally about a vertically disposed axis 72, as required to properly position plate 30 with respect to the edge of a base supporting surface, and the effective length of the table may be adjusted, if required, to properly place plate 30 beneath hand rest 22, by placing bolt 66 in a desired one of a series of openings 28a provided in the table. Also, if desired, the illustrated construction of table mounting means 32 may be replaced by a structure similar to that described for mounting pedestal 36.

In use, constraint 10 is first placed upon a convenient supporting surface, such as a table and then adjusted to accommodate same to the needs of a particular patient and its point of use. In this respect, mounting means 24 and 38 are adjusted as required to increase or decrease the force required to be exerted by a patient to effect swinging movements about axes 26 and 20, respectively, as well as to provide desired spacing of arm rest 22 relative to forearm rest 16 and the latter relative to base 14, and thus to the surface on which the base is placed. The adjusted height of arm rest 16 relative to base 14 will vary depending on the physical size of the patient, whether the patient is in a seated or partially reclined position and differences in elevation between the surfaces supporting the constraint and the patient. Thereafter, mounting means 32 is adjusted to position table 28, and thus plate 30, as required for the convenience of the patient and by the nature of the eating implement to be used.

After adjustment of constraint 10, a patient places, or has placed, his forearm on surface 54 and his hand in hand rest 22; straps 56 are applied for purposes of retaining the patient positioned relative to the constraint; and the handle of an eating implement is placed within recess 22c for retaining engagement by the hand of the patient. The patient may then proceed to feed himself with food placed on plate 30, which normally involves simultaneous swinging movements of hand rest 22 about axes 20 and 26 for purposes of employing the eating implement to pick up and elevate food from the plate to the patient's mouth and to then return the implement to the plate.

While a preferred form of arm constraint has been disclosed, various modifications thereof are presently contemplated. As by way of example, it is contemplated that the plate supporting table can be dispensed with and the plate from which food is to be eaten placed directly on the surface serving to support the base of the constraint.

What is claimed is:

1. A constraint for the arm of a patient subject to uncontrolled tremors to aid in the self-feeding from a food container supported by said constraint, said constraint comprising in combination:
   a base means adapted for mounting on support means;
   a pedestal;
   a first mounting means for mounting said pedestal to upstand from said base means and for rotation relative thereto about a first vertically disposed axis;
   an elongated forearm rest means fixed to an upper end of said pedestal, said forearm rest means defining an upwardly facing horizontally disposed forearm rest surface;
   hand rest means;
   a second mounting means for connecting said hand rest means to one end of said forearm rest means for rotation relative thereto about a second horizontally disposed axis;
   a food container supporting table;
   third mounting means for mounting said table on said base means in an underlying relation to said hand rest means; and
   constraint means for removably retaining a human forearm in engagement with said forearm rest surface with a human hand arranged for overlying engagment with said hand rest means, and said first and second mounting means are individually adjustable for varying the manual force required to rotate said pedestal and said hand rest means about said first and second axes, respectively.

2. A constraint according to claim 1, wherein said hand rest means is provided with an eating implement handle receiving recess extending transversely of said second axis, and said recess is arranged to permit said handle to be retained within said recess by said hand placed on said hand rest means.

3. A constraint according to claim 1, wherein said first mounting means is adjustable to vary the distance between said forearm rest surface and said base means in a direction aligned with said first axis, and said second mounting means is adjustable to vary the distance between said hand rest means and said forearm rest means in a direction aligned with said second axis.

4. A constraint according to claim 1, wherein said forearm rest means includes a first part fixed to said pedestal and connected to said hand rest means by said second mounting means, a second part and means to adjustably fix said second part to said first part to vary the overall length of said forearm rest surface, and said constraint means is carried by said first part.

5. A constraint according to claim 1, wherein said third mounting means is adjustable to vary the vertical distance between said table and said hand rest means.

6. A constraint according to claim 5 wherein said third mounting means is adjustable to vary the position of said table relative to said base means about a third axis disposed parallel to said first axis.

7. A constraint according to claim 5, wherein said hand rest means is provided with an eating implement handle receiving recess extending transversely of said second axis to permit said handle to be retained within said recess by said hand placed on said hand rest means, said second mounting means is adjustable to vary the distance between said hand rest means and said forearm rest means in a direction aligned with said second axis, and said third mounting means is adjustable to vary the position of said table relative to said base means about a third axis disposed parallel to said first axis.

8. A constraint according to claim 7, wherein said forearm rest means includes a first part fixed to said pedestal and connected to said hand rest means by said second mounting means, a second part and means to adjustably fix said second part to said first part to vary the overall length of said forearm rest surface, and said constraint means is carried by said first part.

9. A constraint for the arm of a patient subject to uncontrolled tremors to aid in the self-feeding from a food container supported by said constraint, said constraint comprising in combination:

a base adapted for mounting on a horizontally disposed support means;

forearm rest means defining a forearm rest surface;

means for supporting said forearm rest means on said base for rotation about a first vertically disposed axis and for arranging said rest surface in a horizontally disposed position selectively vertically adjustable relative to said base;

hand rest means;

mounting means for connecting said hand rest means to one end of said forearm rest means for rotation thereto about a second horizontally disposed axis;

a food container supporting table;

table mounting means for mounting said supporting table to said base in an underlying relation to said hand rest means; and constraint means for removably retaining a human forearm in engagement with said rest surface with a human hand arranged for overlying engagement with said hand rest means, and said means for supporting said forearm rest means and said mounting means being selectively individually adjustable for varying the manual force required to rotate said forearm rest means and said hand rest means about said first and second axes, respectively.

10. A constraint according to claim 9, wherein said forearm rest means is adjustable to vary the length of said rest surface.

* * * * *